United States Patent
Cheng et al.

(10) Patent No.: US 8,105,334 B2
(45) Date of Patent: Jan. 31, 2012

(54) LASER-RESISTANT BASKET

(75) Inventors: Eric Cheng, Bloomington, IN (US);
Arthur Butcher, Wellesley, MA (US);
Jeffrey Smith, Poland, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 204 days.

(21) Appl. No.: 12/168,974

(22) Filed: Jul. 8, 2008

(65) Prior Publication Data

US 2009/0069820 A1 Mar. 12, 2009

Related U.S. Application Data

(60) Provisional application No. 60/960,042, filed on Sep. 12, 2007.

(51) Int. Cl.
*A61B 17/22* (2006.01)
(52) U.S. Cl. ....................................................... 606/127
(58) Field of Classification Search .................. 606/110, 606/113, 114, 127, 128, 200
See application file for complete search history.

(56) References Cited

U.S. PATENT DOCUMENTS

| | | | |
|---|---|---|---|
| 6,368,328 B1 * | 4/2002 | Chu et al. | 606/114 |
| 2006/0247663 A1 | 11/2006 | Schwartz et al. | |
| 2008/0119869 A1 | 5/2008 | Teague et al. | |

FOREIGN PATENT DOCUMENTS

| | | |
|---|---|---|
| EP | 1 566 148 A | 8/2005 |
| WO | WO 2006/127330 A | 11/2006 |

OTHER PUBLICATIONS

Written Opinion of the International Searching Authority in PCT/US2008/069758, mailed Sep. 25, 2008, 13 pages.

* cited by examiner

*Primary Examiner* — Ryan Severson
*Assistant Examiner* — Jonathan W Miles
(74) *Attorney, Agent, or Firm* — Finnegan Henderson Farabow Garrett & Dunner, L.L.P.

(57) ABSTRACT

A medical device includes a sheath defining a lumen, an elongate member disposed within the lumen, and a basket connected to a distal end of the elongate member and being retractable within and extendable from the lumen. The basket includes a plurality of legs. At least one leg of the plurality of legs includes a material that is substantially resistant to Holmium laser energy.

45 Claims, 5 Drawing Sheets

LASER-RESISTANT BASKET

PRIORITY DATA

This application claims the benefit of U.S. Provisional Patent Application No. 60/960,042 filed Sep. 12, 2007, the complete disclosure of which is incorporated by reference herein.

FIELD OF THE INVENTION

This disclosure relates generally to medical devices and, more particularly, to devices for the capture and/or retrieval of objects within a body, such as stones, other calculi, or foreign matter.

BACKGROUND OF THE INVENTION

Retrieval devices have been used to remove stones and other calculi from within the body of a patient. One type of retrieval device includes a sheath, an elongate member extending within and moveable relative to the sheath, and a basket connected to the distal end of the elongate member. The basket may have a number of legs, and may have a collapsed position within the sheath and an expanded position beyond a distal end of the sheath. When the basket is in the expanded position, a targeted stone may be captured within the basket and removed from the body. Some stones, however, may be too large to be removed from the body after being captured within the basket. In this situation, a device, such as a laser fiber or other laser lithotripsy device, may be used to break up the stone while the stone is captured. The stone and/or stone particles may then be removed from the body without harming the surrounding body tissue.

It may be difficult, however, to break up the stone with such a lithotripsy device without accidentally cutting or otherwise damaging the legs of the basket. Such damage may cause the user to lose retention of the stone. Such damage may also make the basket difficult to extract from the body without causing trauma to the surrounding body tissue.

The present disclosure provides retrieval devices and methods of using the same that avoid some or all of the aforementioned shortcomings of existing devices.

SUMMARY OF THE INVENTION

In accordance with an exemplary embodiment of the present disclosure, a medical device includes a sheath defining a lumen, an elongate member disposed within the lumen, and a basket connected to a distal end of the elongate member and being retractable within and extendable from the lumen. The basket includes a plurality of legs. At least one leg of the plurality of legs includes a material that is substantially resistant to Holmium laser energy.

In accordance with certain embodiments of the present disclosure, the device may include one or more of the following features. For example, the material is one of silver and gold, the at least one leg has an outer diameter between approximately 0.001 inches and 0.035 inches, the wavelength of the Holmium laser energy is approximately 2100 nm, and the material has a thickness between approximately 0.0001 inches and approximately 0.0003 inches. In addition, the at least one leg includes a substantially flat surface. The at least one leg also includes a core, and an outer coating over the core and including the material.

In accordance with other embodiments of the present disclosure, the material is disposed on a core of the at least one leg. In such embodiments, the core has a resistance to Holmium laser energy less than a resistance to Holmium laser energy of the material, and the core is made from at least one of stainless steel, cobalt chromium, nickel, titanium, and nitinol, and the material is one of silver and gold.

In accordance with further embodiments of the present disclosure, a portion of the at least one leg is selectively removed. In accordance with still further embodiments of the present disclosure, the basket further includes a component having a resistance to Holmium laser energy that is less than a resistance to Holmium laser energy of the material of the at least one leg, and the material reflects at least approximately 96% of the Holmium laser energy at wavelengths above approximately 2000 nm.

In accordance with a further exemplary embodiment of the present disclosure, a medical device basket includes a plurality of interconnected legs forming a proximal base of the basket and an atraumatic distal tip. Each of the legs includes a material that is substantially resistant to Holmium laser energy.

In accordance with certain embodiments of the present disclosure, the basket may include one or more of the following features. For example, the material is one of silver and gold, each of the legs has an outer diameter between approximately 0.001 inches and 0.035 inches, the wavelength of the Holmium laser energy is approximately 2100 nm, the material has a thickness between approximately 0.0001 inches and approximately 0.0003 inches, and at least one leg of the plurality of legs includes a substantially flat surface.

In accordance with additional embodiments of the present disclosure, at least one leg of the plurality of legs includes an outer coating and a core. In such embodiments, the material includes the outer coating of the at least one leg and the core has a resistance to Holmium laser energy less than a resistance to Holmium laser energy of the outer coating. In addition, the core is made from at least one of stainless steel, cobalt chromium, nickel, titanium, and nitinol, and wherein the outer coating is one of silver and gold.

In accordance with other embodiments of the present disclosure, the material reflects at least approximately 96% of the Holmium laser energy at wavelengths above approximately 2000 nm.

In accordance with another exemplary embodiment of the present disclosure, a method of removing matter from the body of a patient includes providing a medical device including a sheath defining a lumen, an elongate member disposed within the lumen, and a basket connected to a distal end of the elongate member and being retractable within and extendable from the lumen. The basket includes a plurality of legs. At least one leg of the plurality of legs includes a material that is substantially resistant to Holmium laser energy. The method further includes advancing the medical device to a treatment site within the body of the patient, capturing the matter within the basket of the device, reducing the size of the matter, and removing the medical device from the body of the patient.

In accordance with certain embodiments of the present disclosure, the method may include one or more of the following features. For example, the material is one of silver and gold, the at least one leg has an outer diameter between approximately 0.001 inches and 0.035 inches, the wavelength of the Holmium laser energy is approximately 2100 nm, and the at least one leg of the plurality of legs includes a substantially flat surface.

In accordance with further embodiments of the method of the present disclosure, the at least one leg of the plurality of legs includes an outer coating and a core. In such embodiments, the material includes the outer coating of the at least one leg and the core has a resistance to Holmium laser energy less than a resistance to Holmium laser energy of the outer coating. Moreover, the core is made from at least one of stainless steel, cobalt chromium, nickel, titanium, and nitinol, and the outer coating is one of silver and gold.

In accordance with other embodiments of the method of the present disclosure, the material reflects at least approximately 96% of the Holmium laser energy at wavelengths above approximately 2000 nm.

In accordance with further embodiments of the present disclosure, a medical device includes a sheath defining a lumen, an elongate member disposed within the lumen, and a basket connected to a distal end of the elongate member. The basket is retractable within and extendable from the lumen. The basket includes a plurality of legs, a portion of an outer surface of at least one leg of the plurality of legs includes at least one of silver and gold.

In accordance with certain embodiments of the present disclosure, the device may include one or more of the following features. For example, the portion of the outer surface is substantially resistant to Holmium laser energy, the wavelength of the Holmium laser energy is approximately 2100 nm, and the material has a thickness between approximately 0.0001 inches and approximately 0.0003 inches. In addition, the at least one leg includes a substantially flat surface In accordance with further embodiments of the present disclosure, the at least one leg includes an outer coating disposed on a core of the at least one leg, and the portion of the outer surface includes a portion of the outer coating. In such embodiments, the core has a resistance to Holmium laser energy less than a resistance to Holmium laser energy of the outer coating. In addition, the core is made from at least one of stainless steel, cobalt chromium, nickel, titanium, and nitinol.

In accordance with further embodiments of the present disclosure, a medical device basket includes a plurality of interconnected legs forming a proximal base of the basket and an atraumatic distal tip. A portion of an outer surface of each of the legs includes at least one of silver and gold.

In accordance with certain embodiments of the present disclosure, the basket may include one or more of the following features. For example, the portion of the outer surface is substantially resistant to Holmium laser energy, the wavelength of the Holmium laser energy is approximately 2100 nm, and the material has a thickness between approximately 0.0001 inches and approximately 0.0003 inches. In addition, the at least one leg includes a substantially flat surface.

In accordance with further embodiments of the present disclosure, the at least one leg includes an outer coating disposed on a core of the at least one leg, and the portion of the outer surface includes a portion of the outer coating. In such embodiments, the core has a resistance to Holmium laser energy less than a resistance to Holmium laser energy of the outer coating. In addition, the core is made from at least one of stainless steel, cobalt chromium, nickel, titanium, and nitinol.

In accordance with another exemplary embodiment of the present disclosure, a method of removing matter from the body of a patient includes providing a medical device including a sheath defining a lumen, an elongate member disposed within the lumen, and a basket connected to a distal end of the elongate member and being retractable within and extendable from the lumen. The basket includes a plurality of legs, and a portion of an outer surface of at least one leg of the plurality of legs includes at least one of silver and gold. The method further includes advancing the medical device to a treatment site within the body of the patient, capturing the matter within the basket of the device, and reducing the size of the matter. The method also includes removing the medical device from the body of the patient.

In accordance with certain embodiments of the present disclosure, the method may include one or more of the following features. For example, the portion of the outer surface is substantially resistant to Holmium laser energy, the wavelength of the Holmium laser energy is approximately 2100 nm, and the material has a thickness between approximately 0.0001 inches and approximately 0.0003 inches. In addition, the at least one leg includes a substantially flat surface.

In accordance with other embodiments of the method of the present disclosure, the at least one leg includes an outer coating disposed on a core of the at least one leg, and the portion of the outer surface includes a portion of the outer coating. In such embodiments, the core has a resistance to Holmium laser energy less than a resistance to Holmium laser energy of the outer coating. In addition, the core is made from at least one of stainless steel, cobalt chromium, nickel, titanium, and nitinol.

It is to be understood that both the foregoing general description and the following detailed description are exemplary and explanatory only, and are not restrictive of the invention as claimed.

DETAILED DESCRIPTION

Exemplary embodiments of the present disclosure are illustrated in the accompanying drawings. Wherever possible, the same reference numbers will be used throughout the drawings to refer to the same or like parts.

Figure 1:
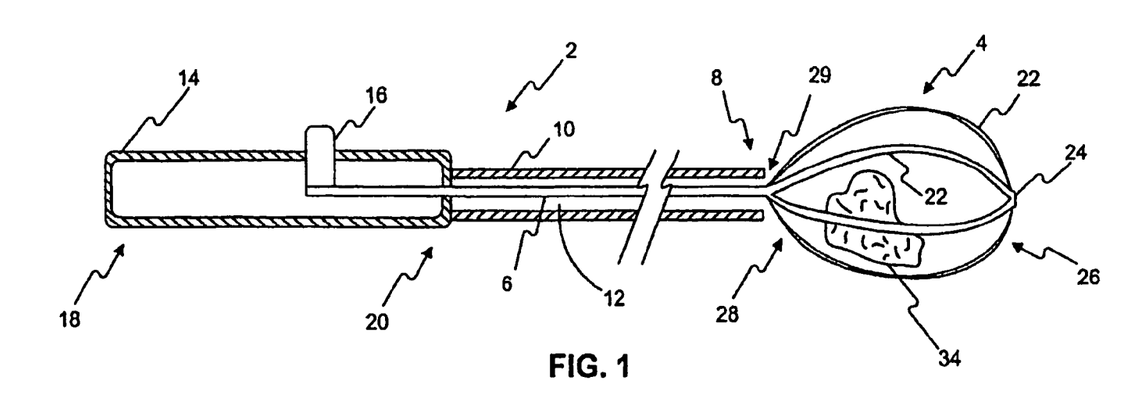
FIG. 1 is a partial cross-sectional view of a retrieval device according to an exemplary embodiment of the present disclosure.

FIG. 1 illustrates a retrieval device 2 according to an exemplary embodiment of the present disclosure. The device 2 includes a basket 4 connected to an elongate member 6. The device 2 further includes a sheath 10 defining a lumen 12, and the elongate member 6 is disposed within the lumen 12. Relative movement between the elongate member 6 and the sheath 10 assists the basket 4 in forming an expanded position (shown in FIG. 1) where the basket 4 is disposed substantially completely beyond a distal end 8 of the sheath 10, and a retracted position (shown in FIG. 2) where the basket 4 is disposed substantially completely within the lumen 12 of the sheath 10.

Figure 2:
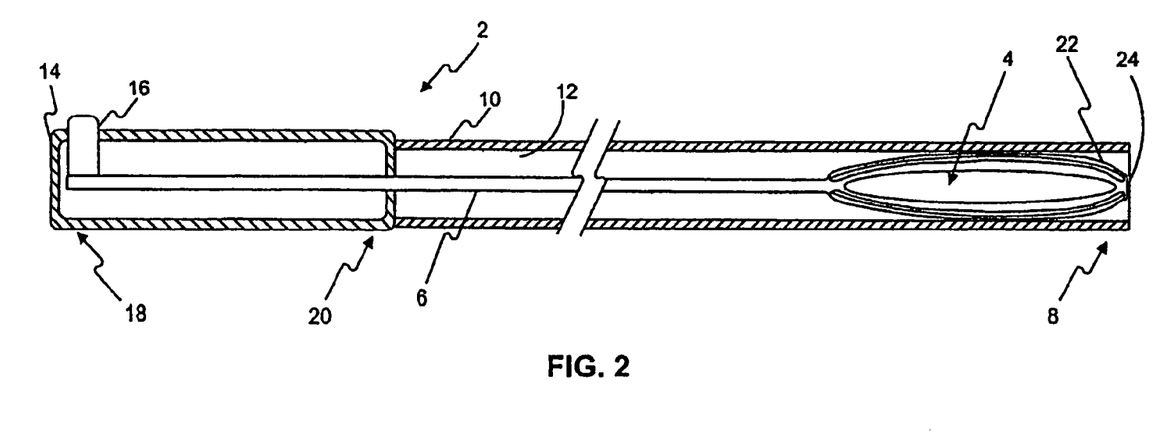
FIG. 2 illustrates an alternate configuration of the device of FIG. 1.

The basket 4 may include a plurality of legs 22. The legs 22 and, thus, a proximal end 28 of the basket 4 may be connected to a distal end 29 of the elongate member 6 in any conventional way. For example, the legs 22 may be made of separate pieces of material that are welded, glued, braided, soldered, and/or otherwise connected to the distal end 29 of the elongate member 6. Alternatively, in another exemplary embodiment, the legs 22 may be formed of the same piece or pieces of material as the elongate member 6. Although FIGS. 1 and 2 show a basket 4 having four legs 22, other exemplary embodiments of the basket 4 may include more or fewer than four legs 22 to facilitate the retrieval of a stone 34, calculi, or other foreign matter.

In an exemplary embodiment, the legs 22 may be looped, knotted, tied, braided, soldered, welded, glued, and/or otherwise joined at a distal end 26 of the basket 4, and the distal end 26 may define an atraumatic tip 24. The atraumatic tip 24 may be blunt, rounded, flat, smooth, knotted, looped, or any other atraumatic shape known in the art. The atraumatic tip 24 may be sized to assist in the capture and retrieval of stones 34 within the body. For example, the atraumatic tip 24 may be as small as possible so as not to interfere with the capture and retrieval of the targeted stone 34. In an exemplary embodiment, the legs 22 of the basket 4 may form the atraumatic tip 24. In an alternative embodiment, the atraumatic tip 24 may comprise, for example, a cap.

The device 2 may further include a handle 14 configured to assist in transitioning the basket 4 between the expanded position and the retracted position. The handle 14 may include, for example, a thumb slide 16 and/or other conventional mechanisms configured to assist in manipulating the position of the basket 4. In an exemplary embodiment, moving the thumb slide 16 toward a distal end 20 of the handle 14 may move the elongate member 6 and the basket 4 in a distal direction relative to the handle 14 and, thus, assist in transitioning the basket 4 to the expanded position shown in FIG. 1. In such an embodiment, moving the thumb slide 16 toward a proximal end 18 of the handle 14 may move the elongate member 6 and the basket 4 in a proximal direction relative to the handle 14 and, thus, assist in transitioning the basket 4 to the retracted position shown in FIG. 2. In this exemplary embodiment, the sheath 10 may remain stationary with respect to the handle 14. In an additional exemplary embodiment, the elongate member 6 and the basket 4 may remain stationary with respect to the handle 14, and the thumb slide 16 may be configured to move the sheath 10 relative to the basket 4. In such an embodiment, moving the thumb slide 16, for example, toward the distal end 20 of the handle 14 may move the sheath 10 in a distal direction relative to the basket 4 and, thus, assist in transitioning the basket 4 to the retracted position. In still another exemplary embodiment, the device 2 may include one or more additional thumb slides (not shown) or other conventional mechanisms to assist in transitioning the basket 4 between the expanded and retracted positions. Such additional mechanisms may be operatively connected to the basket 4 and may be useful, for example, with embodiments of the basket 4 in which the legs 22 are made from relatively low shape memory material.

The elongate member 6 may be formed from, for example, a wire, rod, tube, hypotube, cannula, stent, or other piece of biocompatible material or combination of biocompatible materials known in the art. Such materials may include, but are not limited to, polyamide, PEBAX, silver, stainless steel (such as 300 and 400 series), cobalt chromium, nickel, titanium, nitinol, thermoforming plastic, polytetrafluoroethylene ("PTFE"), and expanded polytetrafluoroethylene ("ePTFE"). The elongate member 6 may also be a metal coated with a polymer and may have one or more layers of material. The elongate member 6 may be solid or hollow, and may be substantially cylindrical. Alternatively, the elongate member 6 may be formed from a flat sheet of material. If formed from a flat sheet, the elongate member 6 may be formed into a substantially cylindrical shape.

The overall length and diameter of the elongate member 6 may vary depending on the application. For example, a relatively long elongate member 6 may be advantageous for retrieving stones 34 or other calculi deep within the body of the patient. In addition, an elongate member 6 having a relatively small diameter may be advantageous for retrieving stones 34 from restricted passageways within the human urinary tract. The elongate member 6 may be relatively flexible to facilitate the retrieval of stones 34 located in complex body structures.

The sheath 10 may be formed from any of the materials discussed above with respect to the elongate member 6. Although FIGS. 1 and 2 illustrate a sheath 10 having a single lumen 12, in additional exemplary embodiments of the present disclosure, the sheath 10 may define more than one lumen 12. The sheath 10 may be dimensioned to fully enclose the elongate member 6 and the basket 4 when the basket 4 is in the retracted position shown in FIG. 2.

As will be described further herein, the legs 22 of the basket 4 may be made, at least in part, from a biocompatible metal or metal alloy known in the art, such as, for example, stainless steel, cobalt chromium, nickel, titanium, and nitinol. Such materials may have a high tensile strength and a high shape memory relative to other conventional biocompatible materials. In addition, the legs 22 of the basket 4 may be made, at least in part, from materials having a relatively high resistance to laser energy. Such materials may include any of the metals or metal alloys listed above, and may further include, in particular preferred embodiments, silver and gold. As will be discussed below, legs 22 made from such materials may reflect laser energy produced, emitted, focused, and/or otherwise directed by a laser source, such as, for example, a Holmium laser, and the legs 22 may resist breakage when laser energy is delivered in close proximity thereto. In an exemplary embodiment, legs 22 made from one of silver and gold may have an outer diameter between approximately 0.001 inches and 0.035 inches.

Each of the legs 22 may be discrete wires, fibers, strands, filaments, or like elongate structures that are joined together to form the basket 4. Alternatively, the legs 22 may be cut, etched, removed, stamped, and/or otherwise formed from a single piece of material.

Figure 3:
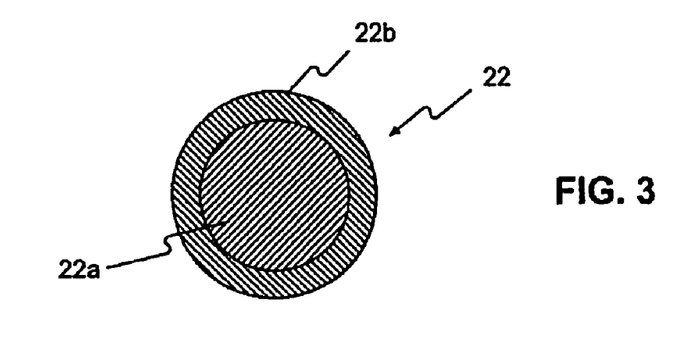
FIG. 3 is a cross-sectional view of a basket leg according to an exemplary embodiment of the present disclosure.
Figure 4:
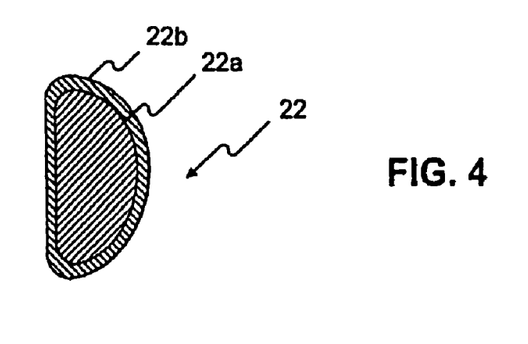
FIG. 4 is a cross-sectional view of a basket leg according to another exemplary embodiment of the present disclosure.
Figure 5:
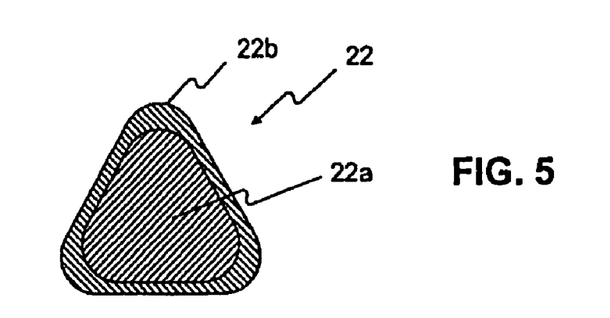
FIG. 5 is a cross-sectional view of a basket leg according to still another exemplary embodiment of the present disclosure.
Figure 6:
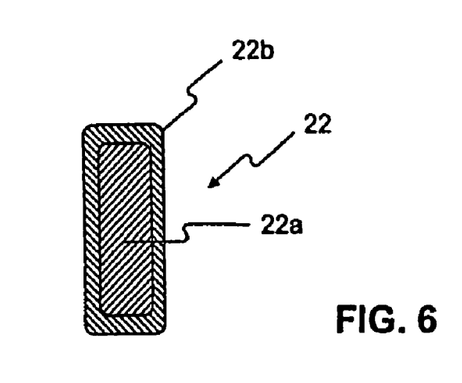
FIG. 6 is a cross-sectional view of a basket leg according to yet another exemplary embodiment of the present disclosure.

The legs 22 may be of any cross-sectional shape known in the art. Such shapes may include, for example, substantially circular (FIG. 3), substantially D-shaped (FIG. 4), substantially triangular (FIG. 5), and substantially rectangular (FIG. 6). In an exemplary embodiment, legs 22 having at least one flat side may exhibit improved reflective qualities and may be more resistant to breakage due to laser energy relative to substantially round legs 22. A flat side of the legs 22 may be positioned on, for example, the inside of the basket 4 and may increase the surface area useful in gripping, holding, capturing, and/or otherwise immobilizing a stone. In another exemplary embodiment, the legs 22 may include at least one sharpened edge (not shown) useful in, for example, fracturing, slicing, and/or otherwise reducing the size of a stone. All of the basket legs 22 may have the same cross-sectional shape. Alternatively, at least one of the legs 22 may have a different cross-sectional shape than the remainder of the basket legs 22.

As shown in FIGS. 3-6, at least one of the legs 22 of the basket 4 may include a core 22a and an outer coating 22b. The core 22a may be made from any of the biocompatible materials discussed above with respect to the legs 22 and, in an exemplary embodiment, the core 22a may be made from metals or metal alloys having a high tensile strength and/or a high shape memory relative to other conventional biocompatible materials. The outer coating 22b may be made from materials having a relatively high resistance to laser energy. As discussed below, silver has been found to be a preferred material for resisting laser energy, especially in medical retrieval applications. Gold also has shown the ability to resist laser energy. In an exemplary embodiment, the legs 22 may be made from, for example, silver, gold, and/or other materials having a relatively high resistance to laser energy, and, in such embodiments, the outer coating 22b may be omitted.

The outer coating 22b may be bonded, adhered, fused, electroplated, and/or otherwise connected to the core 22a to form a single leg 22. The outer coating 22b may be of any desirable thickness. In an exemplary embodiment, the thickness of the coating may be selected so as not to substantially reduce the flexibility of the coated leg 22. In such an exemplary embodiment, the outer coating 22b may have a thickness between approximately 0.0001 inches and approximately 0.0003 inches. In another exemplary embodiment, each of the legs 22 of the basket may include a core 22a and an outer coating 22b.

Figure 7:
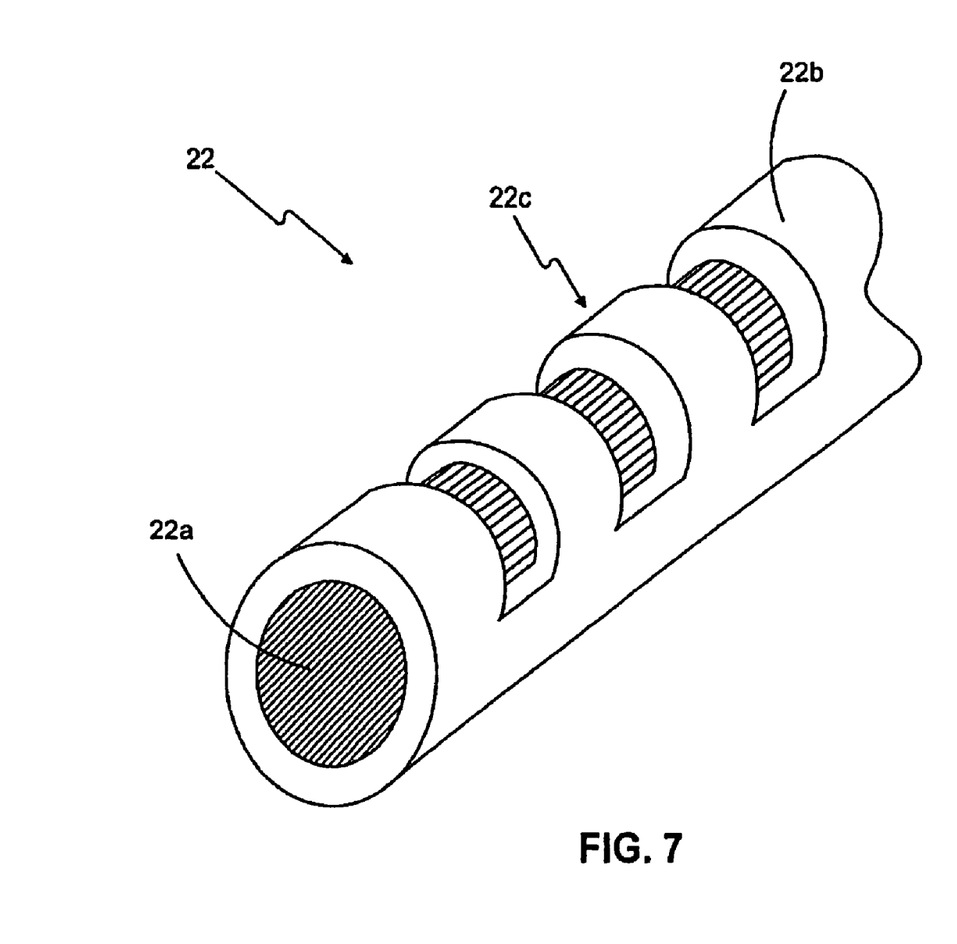
FIG. 7 is a partial cutaway view of a basket leg according to an exemplary embodiment of the present disclosure.

In an exemplary embodiment of the basket 4, at least one of the legs 22 may be selectively etched in any suitable configuration. In an embodiment in which the at least one leg 22 does not include an outer coating 22b, selectively etching the leg 22 may remove at least a portion of the leg 22. In an embodiment in which the at least one leg 22 includes a core 22a and an outer coating 22b (FIGS. 3-6), on the other hand, selectively etching the leg 22 may remove at least a portion of the outer coating 22b and/or may expose at least a portion of the core 22a. Such an exemplary selectively etched leg 22 of the present disclosure is illustrated in FIG. 7. Selectively etching one or more basket legs 22 may produce a basket 4 having desired flexibility, shape memory, strength, and/or other characteristics. The legs 22 may be, for example, selectively etched in a substantially circumferentially grooved configuration, a substantially spiral configuration, and/or any other configuration known in the art. As shown in FIG. 7, partial circumferential grooves selectively etched at one side surface of leg 22 may form an inner surface 22c of the leg 22 that has teeth, spikes, treads, serrations, and/or other structures or textures to aid in gripping a stone 34. Such structures or textures may also provide multipoint contact with a stone 34 and may be pointed away from sensitive tissue within the body of the patient so as not to cause trauma thereto. Such structures or textures may additionally include one or more sharp edges useful in cutting, breaking, and/or otherwise reducing the size of a captured stone 34. Selectively etching at least one of the legs 22 may also increase the flexibility of the at least one leg 22 and/or the basket 4. The at least one leg 22 may be selectively etched through any conventional etching process, such as, for example, mechanical etching, chemical etching, and laser etching.

In an additional exemplary embodiment, a component of the device 2 may be particularly susceptible to breakage when acted upon by laser energy. The susceptible component may be, for example, a portion of one of the legs 22 of the basket 4 or a distal portion of the elongate member 6. In an exemplary embodiment, the susceptible component may be a portion of at least one leg 22, where substantially all of the outer coating 22b has been removed and the core 22a of the portion of the at least one leg 22 is substantially completely exposed. The susceptible component may facilitate, for example, breakage and/or release of the basket 4, as desired by the operator, so that the device 2 may be removed from the body of a patient without causing trauma to surrounding body tissue. The susceptible component may also facilitate, for example, release of a stone 34 captured within the basket 4.

At least the core 22a of each leg 22 may be cold worked or heat processed to form a shape in memory. The shape may be fully formed when the basket 4 is fully expanded. Alternatively, the shape may be partially formed when the basket 4 is partially expanded. The resulting basket 4 may be any shape useful in capturing and/or retrieving a stone 34. Such shapes may include, for example, substantially spherical and substantially lemon-shaped. Although not shown, in addition to the outer coating 22b described above, at least a portion of at least one of the legs 22 of the basket 4 may be coated with, for example, a layer of PTFE, ePTFE, polyvinylethylene, or other material to further protect the legs 22 during processes, such as, for example, laser lithotripsy.

Figure 8:
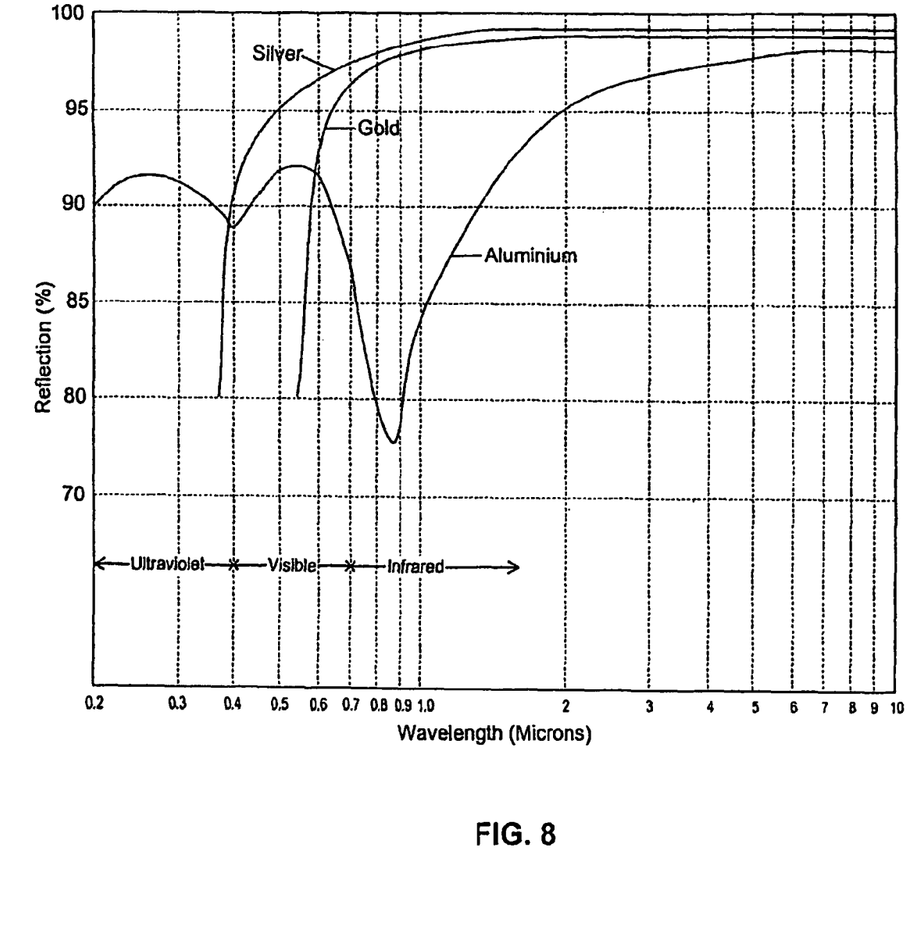
FIG. 8 is an exemplary plot illustrating the optical reflectivity of silver, gold, and aluminum.

As discussed above, certain metals, such as silver and gold, may have high optical reflectivity relative to other metals and metal alloys. As shown in FIG. 8, gold and silver may reflect both visible and infrared light. In particular, at wavelengths above approximately 2 microns (approximately 2000 nm), gold may reflect about 96% of all light energy and silver may reflect approximately 97%-98% of all light energy. Conventional laser sources, such as, for example, laser fibers or other conventional devices used in laser lithotripsy processes, may take advantage of this property by using "half-silvered" mirrors in the interior of the device. Such devices may include, for example, Holmium lasers, ND YAG lasers, CO2 dialed lasers, and/or Candella lasers. The silver portion of the mirror may reflect back the laser light, causing it to stimulate other electrons to decrease in energy level and emit photons. These emitted photons may reflect off the mirror until they are properly aligned and exit out of the "nonsilvered" portion of the mirror. In this way, silver may be used to stimulate and/or concentrate photons.

To verify the approximate optical reflectivity levels of silver illustrated in FIG. 8 (approximately 97%-98% reflective of all light energy), a series of tests were performed using Holmium laser light having a wavelength of approximately 2.1 microns (approximately 2100 nm). As will be discussed below, the results confirm the advantages of using components made from silver (such as, for example, legs 22 made from silver or legs 22 having a silver outer coating 22b) for lithotripsy procedures in which Holmium laser energy is utilized. In particular, the test results illustrate that the reflective properties of silver are adequate to provide basket components, such as, for example, legs 22, with substantial resistance to damage and/or breakage.

Table 1 shows the results of a first test in which three samples of silver wire and one sample of nitinol wire were placed in a testing tank filled with water, submerged, and fired upon with a Holmium laser.

TABLE 1

| Material | OD (inches) | Results of Lasering |
| --- | --- | --- |
| Silver | 0.005 | wire broke |
|  | 0.010 | wire broke |
|  | 0.032 | no damage |
| Nitinol | 0.010 | wire broke |

As illustrated in Table 1, the 0.032-inch silver wire appeared to be substantially laser resistant. Although the smaller diameter silver wire (0.010 inch and 0.005 inch) was broken, it appeared to be more resistant to the laser energy than the nitinol wire.

Table 2 shows the results of a second test in which a sample of 0.010-inch silver wire was flattened to a thickness of 0.003 inches. This piece was then placed in a testing tank filled with water, submerged, and fired upon with a Holmium laser. A piece of 0.010-inch-round nitinol wire was also submerged and fired upon to ensure proper laser functioning. Both samples were fired upon from directly above and from the side.

TABLE 2

| Material | Size (inches) | Results of Lasering |
| --- | --- | --- |
| Silver | 0.003 (thickness) | no damage |
| Nitinol | 0.010 (OD) | wire broke immediately |

As illustrated in Table 2, the 0.003-inch flattened silver wire appeared to be substantially laser resistant, and the laser was unable to mark the wire. The 0.010-inch-round nitinol wire, on the other hand, broke immediately, indicating that nitinol may be inferior to silver, even when the nitinol wire used is thicker than the silver wire.

Table 3 shows the results of a third test in which a sample of 0.032-inch silver wire was flattened to a thickness of 0.012 inches and a width of 0.067 inches. This piece was then placed in a testing tank filled with water, submerged, and fired upon with a Holmium laser. Attempts were made to fire upon the wire from directly above and from the side.

TABLE 3

| Material | Size (inches) | Results of Lasering |
| --- | --- | --- |
| Silver | 0.012 × 0.067 | no damage |

As illustrated in Table 3, the flattened silver wire appears to have been substantially laser resistant, as it remained intact and unmarked. In this test, the wire was directly fired upon for approximately 90 seconds.

Table 4 shows the results of a fourth test in which samples of silver-plated copper, gold-plated nitinol, and nitinol were placed in a testing tank filled with water, submerged, and fired upon with a Holmium laser.

TABLE 4

| Material | Size (inches) | Results of Lasering |
| --- | --- | --- |
| Silver-plated copper | 0.010 | no damage |
| Gold-plated nitinol | 0.010 | wire broke |
| Nitinol | 0.010 | wire broke |

As illustrated in Table 4, the 0.010-inch silver-plated copper wire appeared to be substantially laser resistant. The Holmium laser was unable to damage the silver-plated copper wire, even after repeated lasering. The gold-plated nitinol wire offered some laser resistance and withstood firing from the laser for longer than the nitinol wire, but not as long as the silver-plated copper wire. The 0.010-inch nitinol wire broke when fired upon by the Holmium laser.

Table 5 shows the results of a fifth test in which a basket was made from 99.95% pure, round silver wire having a 0.005-inch diameter. The basket contained four wires and was of a zero-tip style. In addition, the basket was assembled into a fully functional device and placed in a scope and ureter model. The basket was then fired upon by a Holmium laser set to a power of 6 W, 6 Hz, and 1.0 J. After lasering for a period of time, no damage was detected, and the power settings on the Holmium laser were boosted to 10 W, 10 Hz, and 1.0 J.

TABLE 5

| Laser Settings | Results of Lasering |
| --- | --- |
| 6 W, 6 Hz, 1.0 J | no damage |
| 10 W, 10 Hz, 1.0 J | wire broke |

As illustrated in Table 5, the silver wire basket was substantially laser resistant at low power settings but was not able to withstand the laser energy at higher settings.

In a sixth test, a basket was made from 99.95% pure, round silver wire having a 0.010-inch diameter. The basket included three wires and had a soldered tip. For the sixth test, the basket was assembled onto a wire and sheath, and back-loaded through a scope. The basket was then placed in a scope and ureter model, and fired upon with a Holmium laser set to a power of 10 W, 10 Hz, and 1.0 J. Repeated firing with a Holmium laser during the sixth test marked the basket wire, but failed to cause the wire to break. Thus, results of the sixth test showed that the wire basket was somewhat, but not completely, laser resistant.

In a seventh test, a sample of 0.005-inch diameter, round silver wire was flattened to a thickness of 0.0015 inches and a width of 0.012 inches. A four-wire basket was then constructed by soldering the flattened wires to form a distal basket tip. The basket was then assembled onto a wire and sheath, and the device was back-loaded through a scope. For the seventh test, the basket was placed in a scope and ureter model, and fired upon by a Holmium laser set to a power of 10 W, 10 Hz, and 1.0J. Although the flattened wire broke immediately when subjected to the Holmium laser energy, the results of the seventh test were ultimately inconclusive. In particular, a basket having silver wires flattened to a thickness of 0.0015 inches and a width of 0.012 inches may not be laser resistant. Alternatively, due to the relatively extreme thickness of the flattened wires tested, the resulting breakage may have been caused by the shock waves generated by the laser.

Table 6 shows the results of an eighth test in which a piece of 0.010-diameter, round, silver-plated copper wire (having a plating thickness of 6.1%) was used to make a basket-like device having one loop. The device was assembled onto a wire and sheath, and back-loaded through a scope. The device was then placed in a scope and ureter model, and fired upon by a Holmium laser set to a power of 10 W, 10 Hz, and 1.0J.

TABLE 6

| Laser Settings | Results of Lasering |
| --- | --- |
| 10 W, 10 Hz, 1.0 J | no damage |

As illustrated in Table 6, the silver-plated copper device of the eighth test appeared to be substantially laser resistant. After repeated direct hits with the Holmium laser, the device remained intact and substantially unmarked.

Based on the results of the tests discussed above, the reflective properties of silver provide substantial resistance to breakage by laser devices, such as a Holmium laser, particularly relative to nitinol. Thus, silver provides significant laser resistance to basket wires useful in laser lithotripsy procedures. This appears to be true for both substantially pure silver and silver-plated wires. Gold-plated wires also exhibit laser resistance characteristics superior to the nitinol wires tested. In addition to the tabulated results, the testing also evidenced a significant scattering of the laser light in virtually all directions when the laser was focused on the silver wires.

Figure 9:
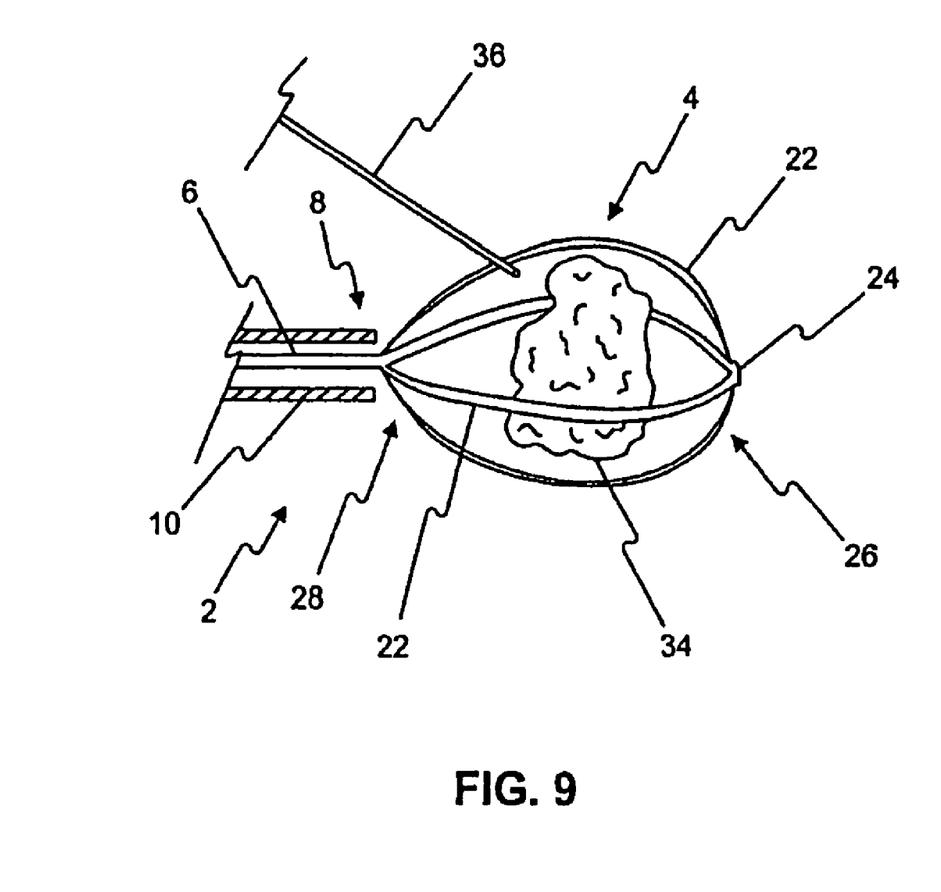
FIG. 9 is a partial view of the retrieval device of FIG. 1.

As illustrated in FIG. 9, devices of the present disclosure may be used, for example, to retrieve a stone 34, calculus, or other material from any location within the body, such as, for example, in the urinary tract of the patient. The retrieval device 2 may be inserted through the urethra of the patient or, alternatively, the device 2 may be inserted percutaneously to a treatment site. The treatment site within the body may correspond to the location of a targeted stone 34.

The stone 34 targeted for retrieval may be a kidney stone, a struvite, a uric acid stone, a cystine stone, or other solid deposit commonly removed from a body structure or passageway within the body. Such stones 34 may contain various combinations of chemicals, including, but not limited to, calcium, oxalate, and phosphate. The stone 34 may be of any size and could have a length or diameter of approximately 1 mm to 12 mm. These lengths and diameters are merely exemplary, and aspects of the present disclosure may assist in the retrieval of stones larger or smaller than those discussed herein. Stones 34 may be of any shape and could be, for example, flat, round, smooth, or jagged. The device 2 may retrieve stones 34 that are both impacted and free floating.

The device 2 may be advanced to the treatment site through an access sheath, stent, or other access or dilatation device known in the art. In addition, the device 2 may be used in conjunction with an endoscope (not shown) or other type of intracorporeal scope known in the art. The endoscope may advance through the body over a guidewire to the treatment site. Alternatively, the endoscope may be independently fed to the treatment site without the use of a guidewire. Once the treatment site has been reached, the device 2 may be fed through an access port of the endoscope to gain access to the stone 34.

While being advanced to the treatment site, the basket 4 of the device 2 may be at least partially, and preferably fully, enclosed within the elongate member 6. This configuration (shown in FIG. 2) may minimize the size of the device 2 and may assist in advancing the device 2 through the endoscope. Upon exiting the endoscope and accessing the stone 34, the user may extend at least a portion of the basket 4 from the distal end 8 of the sheath 10. The basket 4 may then be manipulated relative to the stone 34 so as to capture the stone 34 within the basket 4. Once captured, the stone 34 may be retrieved by removing the device 2 from the body of the patient.

If, however, the targeted stone 34 is larger than approximately 3 mm, the stone 34 may be too large to be safely removed from the body. In these situations, the user may use the device 2 to capture and assist in immobilizing the stone 34. The user may then perform a stone-reduction process, such as, for example, laser lithotripsy, to break up or otherwise reduce the size of the stone 34. The device 4 may act as a backstop during such a process and may assist in preventing particles of the stone 34 from migrating or escaping from the treatment site during or after the stone-reduction process.

As shown in FIG. 9, a laser source, such as, for example, a laser fiber 36 or other conventional device, may be used to break up the stone 34. As discussed above, such devices may include, for example, a Holmium laser, an ND YAG laser, a CO2 dialed laser, a Candella laser, and/or any other laser source known in the art, and such devices may emit laser energy having any wavelength, frequency, and/or amplitude useful in laser lithotripsy procedures. In an exemplary embodiment, the laser fiber 36 may emit laser energy having a wavelength of approximately 2.1 microns (approximately 2100 nm). Laser energy emitted at such wavelengths may be powerful enough to damage and/or break the legs of conventional baskets when emitted in close proximity to the legs. Such a device may also be difficult to use accurately within difficult-to-reach spaces, such as, for example, body structures or passageways within the body of a patient. Thus, it may be common to accidentally direct laser and/or other energy onto the legs 22 of the basket 4 while performing the stone-reduction process, thereby damaging and/or breaking the legs 22. The leg configurations discussed above, such as, for example, legs 22, including silver, gold, and/or other laser-reflective metals or metal alloys, may assist in maintaining the integrity of the basket 4 if laser energy impinges on one or more of the legs 22. In particular, exemplary legs 22 made entirely from silver or gold, or legs 22 including an outer coating 22b made from silver or gold may be substantially resistant to damage and/or breakage when exposed to Holmium laser energy having a wavelength of, for example, approximately 2.1 microns (approximately 2100 nm). Such exemplary legs 22 may exhibit improved Holmium laser resistance and/or reflectivity when at least one side of the legs 22 is substantially flat.

The laser fiber 36 may be fed through an access port of an endoscope and may be activated and controlled by the user to reduce the size of the stone 34 or to fragment it into smaller pieces. A proximal end of the laser fiber 36 may connect to a power source (not shown). Once the stone 34 has been reduced, the device 2 may act as a sweeping device to sweep stones and stone particles obtained from the reduction process out of the body.

Other embodiments of the invention will be apparent to those skilled in the art from consideration of the specification and practice of the invention disclosed herein. For example, foam, mesh, webbing, or some other material may be attached to a number of the legs 22 to assist in the capture, retrieval, or immobilization of a stone 34. It is intended that the specification and examples be considered as exemplary only, with the true scope and spirit of the invention being indicated by the following claims.

What is claimed is:

1. A medical device, comprising:
   a sheath defining a lumen;
   an elongate member disposed within the lumen; and
   a basket connected to a distal end of the elongate member and being retractable within and extendable from the lumen, the basket including a plurality of legs, at least one leg of the plurality of legs including an inner core having an outer surface and an outer core covering the inner core, the outer core comprising a material that is substantially resistant to Holmium laser energy, wherein the outer core is fixed from sliding motion relative to the inner core in an expanded configuration and a retracted configuration of the basket,
   wherein the at least one leg of the plurality of legs includes a first portion, a second portion, and a third portion, wherein, in the first portion of the at least one leg of the plurality of legs, the outer core completely surrounds the outer surface of the inner core, in the second portion of the at least one leg of the plurality of legs, the outer core partially surrounds the outer surface of the inner core, and in the third portion of the at least one leg of the plurality of legs, the outer core completely surrounds the outer surface of the inner core, wherein the second portion is between the first portion and the third portion.

2. The medical device of claim 1, wherein the material comprises one of silver and gold.

3. The medical device of claim 2, wherein the at least one leg has an outer diameter between approximately 0.001 inches and 0.035 inches.

4. The medical device of claim 1, wherein the wavelength of the Holmium laser energy is approximately 2100 nm.

5. The medical device of claim 1, wherein the outer core has a thickness between approximately 0.0001 inches and approximately 0.0003 inches.

6. The medical device of claim 1, wherein the at least one leg includes a substantially flat surface.

7. The medical device of claim 1, wherein the inner core has a resistance to Holmium laser energy less than a resistance to Holmium laser energy of the material.

8. The medical device of claim 1, wherein the inner core is made from at least one of stainless steel, cobalt chromium, nickel, titanium, and nitinol, and wherein the material comprises one of silver and gold.

9. The medical device of claim 1, wherein the basket further includes a component having a resistance to Holmium laser energy that is less than a resistance to Holmium laser energy of the material of the at least one leg.

10. The medical device of claim 1, wherein the material reflects at least approximately 96% of the Holmium laser energy at wavelengths above approximately 2000 nm.

11. The medical device of claim 1, wherein a cross-sectional shape of the inner core is substantially circular, and wherein the outer core includes a sharp edge at an intersection of the first portion and the second portion.

12. The medical device of claim 11, wherein the outer core includes a sharp edge at an intersection of the second portion and the third portion.

13. The medical device of claim 1, wherein the partially surrounded outer surface of the inner core of the second portion faces away from a central longitudinal axis of the basket.

14. The medical device of claim 1, wherein the partially surrounded outer surface of the inner core of the second portion faces toward a central longitudinal axis of the basket.

15. The medical device of claim 1, wherein a radius of curvature is substantially constant along an entire outer surface of the outer core at the second portion.

16. The medical device of claim 1, wherein each of the plurality of legs includes an inner core having an outer surface and an outer core covering the inner core, the outer core comprising a material that is substantially resistant to Holmium laser energy, wherein, in a first portion of each leg, the outer core completely surrounds the outer surface of the inner core, in a second portion of each leg, the outer core partially surrounds the outer surface of the inner core, and in a third portion of each leg, the outer core completely surrounds the outer surface of the inner core, wherein the second portion is between the first portion and the third portion.

17. The medical device of claim 1, wherein the outer core is formed of a continuous single piece of material.

18. A medical device basket, comprising:
a plurality of interconnected legs forming a proximal base of the basket and an atraumatic distal tip, at least one leg of the plurality of legs including an inner core having an outer surface and an outer core covering the inner core, the outer core comprising a material that is substantially resistant to Holmium laser energy, wherein the outer core is fixed from sliding motion relative to the inner core in an expanded configuration and a retracted configuration of the basket,
wherein the at least one leg of the plurality of legs includes a first portion, a second portion, and a third portion, wherein, in the first portion of the at least one leg of the plurality of legs, the outer core completely surrounds the outer surface of the inner core, in the second portion of the at least one leg of the plurality of legs, the outer core partially surrounds the outer surface of the inner core, and in the third portion of the at least one leg of the plurality of legs, the outer core completely surrounds the outer surface of the inner core, wherein the second portion is between the first portion and the third portion.

19. The medical device basket of claim 18, wherein the material comprises one of silver and gold.

20. The medical device basket of claim 19, wherein each of the legs has an outer diameter between approximately 0.001 inches and 0.035 inches.

21. The medical device basket of claim 18, wherein the wavelength of the Holmium laser energy is approximately 2100 nm.

22. The medical device basket of claim 18, wherein the outer core has a thickness between approximately 0.0001 inches and approximately 0.0003 inches.

23. The medical device basket of claim 18, wherein at least one leg of the plurality of legs includes a substantially flat surface.

24. The medical device basket of claim 18, wherein the inner core has a resistance to Holmium laser energy less than a resistance to Holmium laser energy of the material.

25. The medical device basket of claim 18, wherein the inner core is made from at least one of stainless steel, cobalt chromium, nickel, titanium, and nitinol, and wherein the material comprises one of silver and gold.

26. The medical device basket of claim 18, wherein the material reflects at least approximately 96% of the Holmium laser energy at wavelengths above approximately 2000 nm.

27. A medical device, comprising:
a sheath defining a lumen;
an elongate member disposed within the lumen; and
a basket connected to a distal end of the elongate member and being retractable within and extendable from the lumen, the basket including a plurality of legs, at least one leg of the plurality of legs including an inner core having an outer surface and an outer core covering the inner core, the outer core comprising at least one of silver and gold, wherein the outer core is fixed from sliding motion relative to the inner core in an expanded configuration and a retracted configuration of the basket,
wherein the at least one leg of the plurality of legs includes a first portion, a second portion, and a third portion, wherein, in the first portion of the at least one leg of the plurality of legs, the outer core completely surrounds the outer surface of the inner core, in the second portion of the at least one leg of the plurality of legs, the outer core partially surrounds the outer surface of the inner core, and in the third portion of the at least one leg of the plurality of legs, the outer core completely surrounds the outer surface of the inner core, wherein the second portion is between the first portion and the third portion.

28. The medical device of claim 27, wherein the outer core is substantially resistant to Holmium laser energy.

29. The medical device of claim 28, wherein the wavelength of the Holmium laser energy is approximately 2100 nm.

30. The medical device of claim 27, wherein the outer core has a thickness between approximately 0.0001 inches and approximately 0.0003 inches.

31. The medical device of claim 27, wherein the at least one leg includes a substantially flat surface.

32. The medical device of claim 27, wherein the inner core has a resistance to Holmium laser energy less than a resistance to Holmium laser energy of the material.

33. The medical device of claim 27, wherein the inner core is made from at least one of stainless steel, cobalt chromium, nickel, titanium, and nitinol.

34. The medical device of claim 27, wherein a cross-sectional shape of the inner core is substantially circular, and wherein the outer core includes a sharp edge at an intersection of the first portion and the second portion.

35. The medical device of claim 27, wherein the partially surrounded outer surface of the inner core of the second portion faces away from a central longitudinal axis of the basket.

36. The medical device of claim 27, wherein a radius of curvature is substantially constant along an entire outer surface of the outer core at the second portion.

37. The medical device of claim 27, wherein each of the plurality of legs includes an inner core having an outer surface and an outer core covering the inner core, the outer core comprising at least one of silver and gold, wherein, in a first portion of each leg, the outer core completely surrounds the outer surface of the inner core, in a second portion of each leg, the outer core partially surrounds the outer surface of the inner core, and in a third portion of each leg, the outer core completely surrounds the outer surface of the inner core, wherein the second portion is between the first portion and the third portion.

38. A medical device basket, comprising:
a plurality of interconnected legs forming a proximal base of the basket and an atraumatic distal tip, at least one leg of the plurality of legs including an inner core having an outer surface and an outer core covering the inner core, the outer core comprising at least one of silver and gold, wherein the outer core is fixed from sliding motion relative to the inner core in an expanded configuration and a retracted configuration of the basket,
wherein the at least one leg of the plurality of legs includes a first portion, a second portion, and a third portion, wherein, in the first portion of the at least one leg of the plurality of legs, the outer core completely surrounds the outer surface of the inner core, in the second portion of the at least one leg of the plurality of legs, the outer core partially surrounds the outer surface of the inner core, and in the third portion of the at least one leg of the plurality of legs, the outer core completely surrounds the outer surface of the inner core, wherein the second portion is between the first portion and the third portion.

39. The medical device basket of claim 38, wherein the outer core is substantially resistant to Holmium laser energy.

40. The medical device basket of claim 39, wherein the wavelength of the Holmium laser energy is approximately 2100 nm.

41. The medical device basket of claim 38, wherein the outer core has a thickness between approximately 0.0001 inches and approximately 0.0003 inches.

42. The medical device basket of claim 38, wherein the at least one leg includes a substantially flat surface.

43. The medical device basket of claim 38, wherein the inner core has a resistance to Holmium laser energy less than a resistance to Holmium laser energy of the material.

44. The medical device basket of claim 38, wherein the inner core is made from at least one of stainless steel, cobalt chromium, nickel, titanium, and nitinol.

45. A medical device, comprising:
a sheath defining a lumen;
an elongate member disposed within the lumen;
a basket connected to a distal end of the elongate member and being retractable within and extendable from the lumen, the basket including a plurality of legs, each leg including an inner core having an outer surface and an outer core covering the inner core, the outer core comprising a material that is substantially resistant to Holmium laser energy, wherein the outer core is fixed from sliding motion relative to the inner core in an expanded configuration and a retracted configuration of the basket; and
wherein the at least one leg of the plurality of legs includes a first portion, a second portion, and a third portion, wherein, in the first portion of each leg, the outer core completely surrounds the outer surface of the inner core, in the second portion of each leg, the outer core partially surrounds the outer surface of the inner core, and in the third portion of each leg, the outer core completely surrounds the outer surface of the inner core, wherein the second portion is between the first portion and the third portion,
wherein a cross-sectional shape of the inner core is substantially circular, and wherein the outer core includes a sharp edge at an intersection of the first portion and the second portion,
wherein the sharp edge faces toward a central longitudinal axis of the basket,
wherein a radius of curvature is substantially constant along an entire outer surface of the outer core at the second portion.

* * * * *